United States Patent [19]

Puhl

[11] 4,357,717
[45] Nov. 9, 1982

[54] SPORTS IMPLEMENT HANDLE-HOLDING ATTACHMENT FOR PROSTHESIS

[76] Inventor: Earl M. Puhl, 3807 S. 18th St., Milwaukee, Wis. 53221

[21] Appl. No.: 234,611

[22] Filed: Feb. 17, 1981

[51] Int. Cl.³ .............................................. A61F 1/06
[52] U.S. Cl. ......................................... 3/12.8; 3/12.4
[58] Field of Search ........................ 3/12.8, 12.4, 12.5, 3/12

[56] References Cited

U.S. PATENT DOCUMENTS

| | | | |
|---|---|---|---|
| 2,561,523 | 7/1951 | Lux | 3/12.8 X |
| 2,566,215 | 8/1951 | La Croix | 3/12.8 |
| 3,266,059 | 8/1966 | Stelle | 3/12.5 X |
| 3,747,128 | 7/1973 | De Filipo | 3/12.8 |
| 3,965,491 | 6/1976 | Frenzel | 3/12.8 |

FOREIGN PATENT DOCUMENTS 161615 12/1957 Sweden ................................. 3/12.8

*Primary Examiner*—Ronald L. Frinks
*Attorney, Agent, or Firm*—Andrus, Sceales, Starke & Sawall

[57] ABSTRACT

The attachment, which is adapted to be connected to a prosthesis at one end and to a sports implement handle at the other end, is provided with a central section of resilient flexible material. The central section is of sufficient stiffness to normally hold the attachment elements in fixed position, but flexes upon swinging of the arm in a manner to produce a universal wrist-type whipping action. The resilient flexible central section is generally bar-like. A first rigid member adapted for attachment with the prosthesis is disposed in telescoping relationship with one end of the central section, while a second rigid member adapted for attachment with the sports implement handle is disposed in telescoping relationship with the other end of the central section. Upon swinging of the implement, the central section freely flexes universally to enable the first and second rigid members to move angularly with respect to one another throughout a range of 360°. The two rigid members are connected together by a further flexible element which serves to relieve outward axial forces on the central section during swinging. A protective cuff may be placed over the attachment to prevent interference between the user's good hand and the attachment during a downswing in golfing.

10 Claims, 4 Drawing Figures

U.S. Patent
Nov. 9, 1982
4,357,717
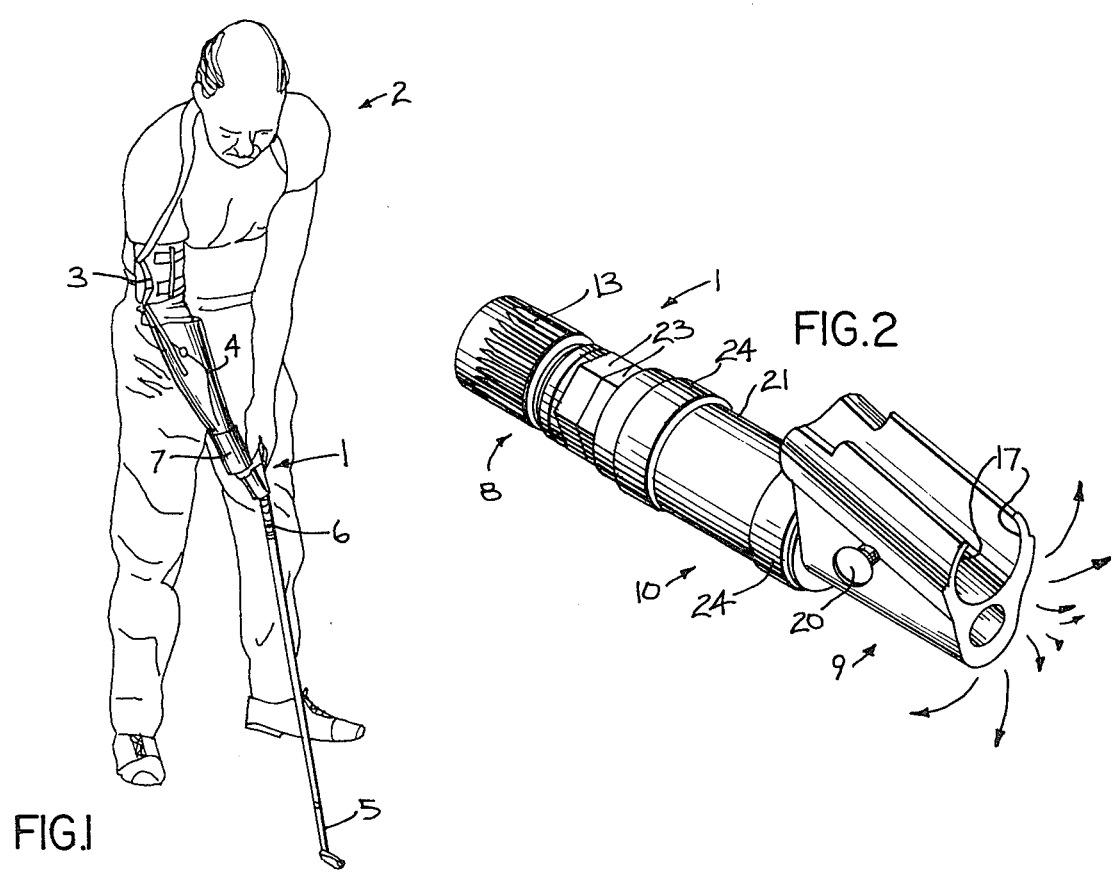
FIG.1
FIG.2
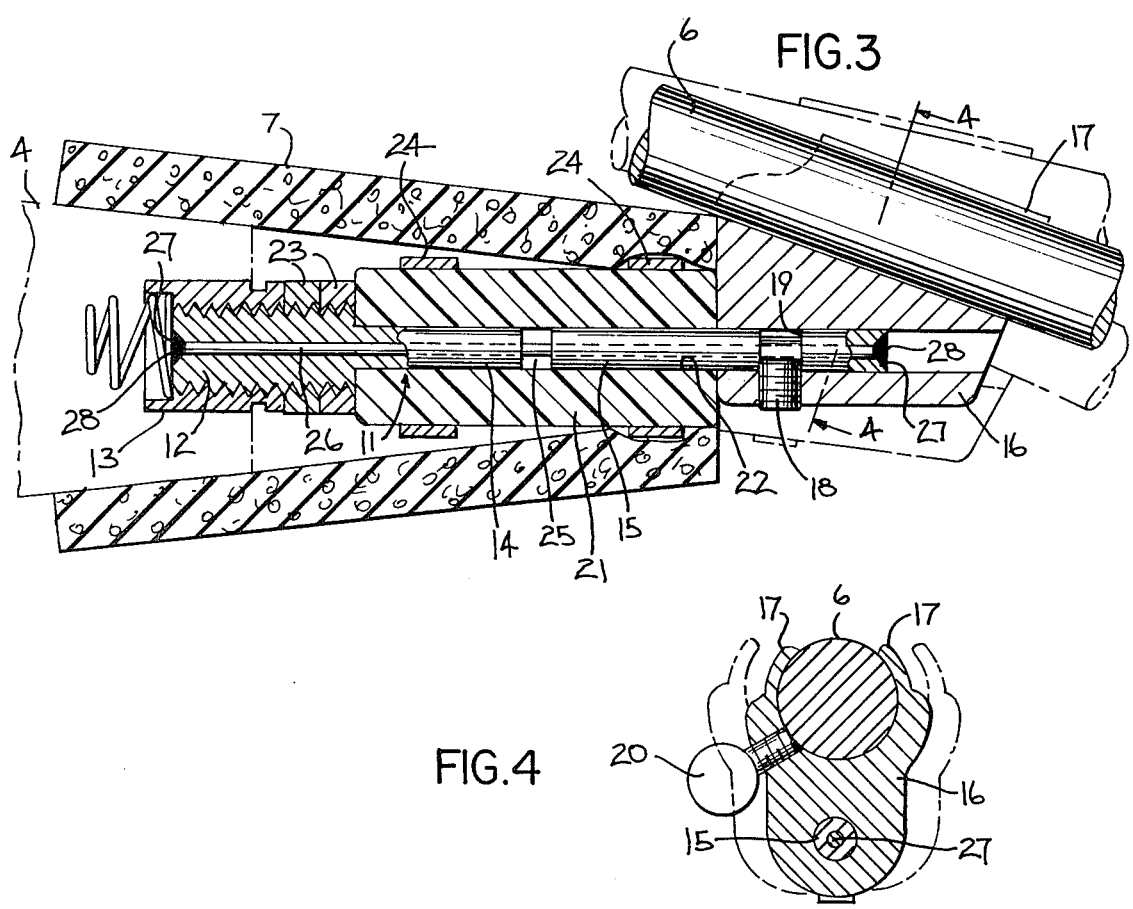
FIG.3
FIG.4

SPORTS IMPLEMENT HANDLE-HOLDING ATTACHMENT FOR PROSTHESIS

U.S. PRIOR ART OF INTEREST

| Number | Inventor | Issue Date |
| --- | --- | --- |
| 2,566,215 | Croix | Aug. 28, 1951 |
| 3,747,128 | De Filipo | July 24, 1973 |
| 3,965,491 | Frenzel | June 29, 1976 |

BACKGROUND AND SUMMARY OF THE INVENTION

This invention relates to a sports implement handle-holding attachment for a prosthesis attached to the remaining stump of an amputee's arm to enable the amputee to make a relatively normal golf or tennis swing. The attachment is primarily intended for those whose arm has been severed below the elbow.

Various attachment devices have previously been suggested for use by amputees to enable them to play golf or the like. But these devices have certain drawbacks which prevent the user from swinging in a truly normal manner. For example, U.S. Pat. No. 3,965,491 shows such a device, but due to its construction the user is limited to swinging the club in a substantially single plane. The same is basically true of the tennis racket adapter of U.S. Pat. No. 2,566,215, and the golf club adapter of U.S. Pat. No. 3,747,128.

To enable an amputee to swing a golf club or tennis racket in a normal fashion, it is desirable to provide a substitute for the usual wrist motion which is critical to proper swinging of the implement.

It is a task of the invention to provide an implement holding attachment for a prosthesis which gives a substantially improved swinging action as compared with prior known devices. It is a further task of the invention to provide such an attachment which substantially simulates the motion of a normal wrist during swinging of the implement.

In accordance with one aspect of the invention, the attachment, which is adapted to be connected to a prosthesis at one end and to a sports implement handle at the other end, is provided with a central section of resilient flexible material. The central section is of sufficient stiffness to normally hold the attachment elements in fixed position, but flexes upon swinging of the arm in a manner to produce a universal wrist-type whipping action.

In accordance with another aspect of the invention, the resilient flexible central section is generally bar-like. A first rigid member adapted for attachment with the prosthesis is disposed in telescoping relationship with one end of the central section, while a second rigid member adapted for attachment with the sports implement handle is disposed in telescoping relationship with the other end of the central section. Upon swinging of the implement, the central section freely flexes universally to enable the first and second rigid members to move angularly with respect to one another throughout a range of 360°.

In accordance with an additional aspect of the invention, the two rigid members are connected together by a further flexible element which serves to relieve outward axial forces on the central section during swinging.

In accordance with yet another aspect of the invention, a protective cuff may be placed over the attachment to prevent interference between the user's good hand and the attachment during a downswing in golfing.

BRIEF DESCRIPTION OF THE DRAWINGS

The accompanying drawings illustrate the best mode presently contemplated by the inventor for carrying out the invention.

In the drawings:

FIG. 1 is a perspective view of a golfer-amputee using the attachment of the invention;

FIG. 2 is a perspective view of the attachment;

FIG. 3 is an enlarged longitudinal section of the attachment, cuff, and a portion of the prosthesis; and FIG. 4 is a transverse section of the attachment taken on line 4—4 of FIG. 3.

DESCRIPTION OF THE PREFERRED EMBODIMENT

Although the attachment of the invention may be used with a sports implement such as a tennis racket, the drawings illustrate the preferred use with a golf club.

The attachment 1 is shown in FIG. 1 as being used by a golfer-amputee 2 whose right arm has been severed below the elbow and who has a control mechanism 3 on his upper arm and a prosthesis 4 attached to his lower arm stump. A golf club 5 having a handle 6 is secured to attachment 1, as will be described, and an auxiliary cuff 7 surrounds at least a portion of the attachment.

As shown in FIGS. 2 and 3, attachment 1 comprises an inner portion 8 and an outer portion 9 which are joined by a central portion 10.

Inner portion 8 is adapted for connection to prosthesis 4 and comprises a rigid elongated rod 11 having an outer threaded end portion 12 which receives thereon the usual adapter member 13 which is latchingly received within a socket in the end of prosthesis 4. Rod portion 12 steps down to a smaller diameter at its approximate midportion and has an inner unthreaded end portion 14 for purposes to be described.

Outer attachment portion 9 is adapted for connection to golf club handle 6 and comprises a second rigid elongated rod 15 shown in this embodiment as being unthreaded and of a uniform diameter similar to the reduced diameter of the first rod's inner portion 14. The outer portion of rod 15 receives thereover a clamp 16 having opposed curved flanges 17 which receive the upper end portion of golf club handle 6. Clamp 16 is fixedly secured to rod 15, as by set screw 18 which engages in a groove 19 in the rod. Likewise, club handle 6 is fixedly secured within the channel formed by flanges 17, as by a set screw 20.

Central portion 10 comprises a connector which telescopingly joins the inner ends of portions 8 and 9. In the present embodiment, the connector comprises an elongated bar 21 having an axial bore 22 extending therethrough to form a sleeve and with the bore tight fittingly receiving the inner unthreaded end portions of rods 11 and 15. Bar 21 is confined between clamp 16 and a pair of rightening nuts 23 disposed on threaded portion 12 of rod 11, and is held in place on rods 11 and 15, as by clamping rings 24.

As shown, bar 21 is relatively thick-walled and the construction is such that rods 11 and 15 are normally positioned co-axially with their opposed facing inner ends being slightly separated to form a space 25 in bore 22.

In accordance with the concepts of the invention, bar 21 is formed of relatively resilient flexible non-rigid material, such as polyurethane. The stiffness of bar 21 should be such that it normally holds rods 11 and 15 in fixed co-axial position. However, when golfer 2 swings club 5, bar 21 will freely flex in the manner of a wrist and in an infinite number of directions throughout 360° to develop the desired whip in the golf club. Bar 21 is permitted to flex by virtue of the discontinuity created by space 25, causing support rods 11 and 15 and their associated assemblages to move angularly relative to each other, and also universally throughout 360°. Reference is made to the arrows in FIG. 2 and the phantom showings in FIGS. 3 and 4 which illustrate flexing of the device.

The flexure characteristics of attachment 1 will depend on the particular composition of bar 21, its thickness and length, the diameter and inserted length of the inner supporting rod portions and the like. It has been found that a 1" diameter bar 21 of polyurethane having an overall length of $2\frac{1}{4}"$ and a bore 22 of $\frac{3}{8}"$ diameter, with rods 11 and 15 extending to about 3/16" of each other, will function very satisfactorily.

During use of the device of the invention, outward axial forces will be applied which may tend to cause portions 8 and 9 to slidingly separate from bar 21. To prevent this, means may be provided to hold the assembly together to thereby relieve bar 21 from the axial forces. For this purpose, rods 11 and 15 are prevented from outward axial movement. In the present embodiment, and referring to FIGS. 3 and 4, a thin flexible thread 26 of wire or the like extends axially and continuously through both rods 11 and 15 as well as space 25, with thread 26 being taut and terminating at the outer ends of the rods. The end faces of rods 11 and 15 are countersunk to form recesses 27, with the respective adjacent thread ends therein, and attachment means such as lead 28 or the like is poured into the recesses to hold thread 26 in place, thus locking the assembly parts so that they cannot axially separate. Thread 26 flexes or bends in space 25 when connector bar 21 flexes.

To prevent possible interference by the golfer's free hand with the flexing operation of attachment 1, a soft protective removable sleeve-like cover in the form of auxiliary cuff 7 may be placed over at least inner and central portions 8 and 10 of the attachment. Cuff 7 is shown as overlapping prosthesis 4 and the joint between the latter and the attachment.

The device of the invention permits an amputee to swing a sports implement in a much more normal fashion than was heretofore possible. It may be easily adapted for use with either the right or left arm.

Various modes of carrying out the invention are contemplated as being within the scope of the following claims particularly pointing out and distinctly claiming the subject matter which is regarded as the invention.

I claim:

1. A sports implement handle-holding attachment for an amputee's prosthesis comprising:
   (a) a rigid inner portion for connection to the prosthesis,
   (b) a rigid outer portion for connection to the sports implement handle,
   (c) and a non-rigid central portion connecting said inner and outer portions in co-axial relationship,
   (d) said central portion being sufficiently stiff to normally hold said inner and outer portions in fixed co-axial positions but being sufficiently flexible so that, during swinging of the implement handle, it will freely flex throughout 360° to provide relative angular movement between said inner and outer portions in a simulated wrist-like action.

2. The attachment of claim 1 wherein said rigid inner and outer portions are telescopingly mounted to said non-rigid central portion.

3. The attachment of claim 2 wherein:
   (a) said central portion comprises an elongated bar having an axial bore extending therethrough,
   (b) and said rigid inner and outer portions each include an elongated rod, with said rods extending into said bore in opposed axial relationship and with the inner rod ends facing each other and spaced apart to facilitate flexing of said central portion.

4. The attachment of claim 3 which includes means confining the ends of said bar between said inner and outer portions.

5. The attachment of claim 3 or 4 which includes clamping means securing said bar to said rods.

6. The attachment of claim 2 which includes means for relieving said flexible central portion from outward axial forces during swinging of the implement handle.

7. The attachment of claim 6 in which said relieving means comprises: means locking said inner and outer portions against axial separation.

8. The attachment of claim 3 which includes means for relieving said bar from outward axial forces, said relieving means comprising:
   (a) a taut continuous thread extending axially through said rods and the space between the said inner rod ends,
   (b) and means securing each end of said thread to the respective adjacent rod to lock said rods against axial separation.

9. The attachment of claim 8 in which said thread end securing means comprises:
   (a) a recess formed in the outer end face of each said rod, and with a thread end disposed in each said recess,
   (b) and attachment means filling said recess.

10. The attachment of claim 1, 3 or 8 which includes means for covering at least said inner and central portions to prevent interference by the amputee's free hand with the flexing of the attachment during swinging of the implement handle.

* * * * *